(12) United States Patent
Larrow et al.

(10) Patent No.: US 6,639,087 B2
(45) Date of Patent: Oct. 28, 2003

(54) KINETIC RESOLUTION METHOD

(75) Inventors: Jay F. Larrow, Wakefield, MA (US); Serge Jasmin, Watertown, MA (US); Yi Liu, Weymouth, MA (US); Marcello Di Mare, Belmont, MA (US)

(73) Assignee: Rhodia Pharma Solutions Inc., Cranbury, NJ (US)

( * ) Notice: Subject to any disclaimer, the term of this patent is extended or adjusted under 35 U.S.C. 154(b) by 0 days.

(21) Appl. No.: 10/225,902

(22) Filed: Aug. 22, 2002

(65) Prior Publication Data

US 2003/0088114 A1 May 8, 2003

Related U.S. Application Data

(60) Provisional application No. 60/314,247, filed on Aug. 22, 2001.

(51) Int. Cl.$^7$ .................. C07D 301/32; B01J 31/22; B01J 31/40
(52) U.S. Cl. .............. 549/541; 549/513; 549/540; 502/150; 502/170; 502/171
(58) Field of Search ................ 549/541, 513, 549/540; 502/150, 170, 171

(56) References Cited

U.S. PATENT DOCUMENTS

| | | | | |
|---|---|---|---|---|
| 5,637,739 A | 6/1997 | Jacobsen et al. | ............ | 549/524 |
| 5,663,393 A | 9/1997 | Jacobsen et al. | ............ | 556/45 |
| 5,665,890 A | 9/1997 | Jacobsen et al. | ............ | 549/230 |
| 5,929,232 A | 7/1999 | Jacobsen et al. | ............ | 540/145 |
| 6,262,278 B1 | 7/2001 | Jacobsen et al. | ............ | 549/230 |
| 6,448,414 B1 | 9/2002 | Jacobsen et al. | ............ | 549/230 |

FOREIGN PATENT DOCUMENTS

| | | | | |
|---|---|---|---|---|
| US | WO 01/89690 A1 | 11/2001 | ............ | B01J/31/00 |
| US | WO 02/48162 A1 | 6/2002 | ............ | C07F/15/00 |

OTHER PUBLICATIONS

Tokunaga, M.; Larrow, J.F.; Kakiuchi, F.; Jacobsen, "Asymmetric Catalysis with Water: Efficient Kinetic Resolution of Terminal Epoxides by Means of Catalytic Hydrolysis," N. Science, 1997, vol. 277, 936–938.

Schaus, S.E.; Brandes, B. D.; Larrow, J.F.; Tokunaga, M.; Hansen, K.B.; Gould, A.E.; Furrow, M.E.; Jacobsen, Highly Selective Hydrolytic Kinetic Resolution of Terminal Epoxides Catalyzed by Chiral (salen)Co "Complexes. Practical Synthesis of Enantioenriched Terminal Epoxides and 1,2–Diols," J. Am. Chem. Soc., 2002, vol. 124, 1307–1315.

Schaus, S.E.; Jacobsen, "Dynamic Kinetic Resolution of Epichlorohydrin via Enantioselective Catalytic Ring Opening with TMSN3. Practical Synthesis of Aryl Oxazolididinone Antibacterial Agents," Tetrahedron Letters, 1996, vol. 37, 7937–7940.

Takeichi, T.; Ishimori, M.; Tsuruta, T., "Asymmetric Cyclization of Propylene Chlorohydrins Catalyzed by an Optically Active Cobalt(salen) Type Complex," Bull. Chem. Soc. Jpn., 1979, vol. 52, 2614–2618.

Takeichi, T.; Arihara, M.; Ishimori, M.; Tsuruta, T. , "Asymmetric Cyclizations of Some Chlorohydrins Catalyzed by Optically Active Cobalt(Salen) Type Complexes," Tetrahedron, 1980,vol. 36, 3391–3398.

Ready, J.M., Jacobsen, E.N., "Highly Active Oligomeric (salen)Co Catalysts for Asymmetric Epoxide Ring Opening Reactions," J. AM. Chem. Soc. 2001, 123, 2687–2688.

Furrow, M.E., Schaus, S.E., Jacobsen, E.N. "Practical Access to Highly Enantioenriched C–3 Building Blocks via Hydrolytic Kinetic Resolution," J. Org. Chem. 1998, 63, 6776.

Ready, Joseph M. Jacobsen, E.N., "A Practical Oligomeric [(salen)Co] Catalyst for Asymmetric Epoxide Ring–Opening Reactions", Angew. Chem. Int. Ed. 2002, 41, No. 8, 1374–1377.

Stinson, Stephen C., "Chiral Drugs", Chem. Eng. News, pp. 46–79, Sep. 28, 1992.

Jacobsen, "Asymmetric Catalysis of Epoxide Ring–Opening Reactions." Acc. Chem. Res. 2000, 33, 421–431.

Annis et al. "Polymer–supported chiral Co(Salen) complexes: Synthetic applications and mechanistic investigations in the hydrolytic kinetic resolution of terminal epoxides." J. Am. Chem. Soc., 121, 4147–4154 (1999).

Ready et al. "Asymmetric Catalytic Synthesis of a–aryloxy Alcohols: Kinetic Resolution of Terminal Epoxides via Highly Enantioselective Ring–Opening with Phenols." J. Am. Chem. Soc. 1999, 121, 6086–6087.

*Primary Examiner*—Ba K. Trinh
(74) *Attorney, Agent, or Firm*—Kevin E. McVeigh

(57) ABSTRACT

A method for stereoselective chemical synthesis, includes the steps of: (A) reacting a nucleophile and chiral or prochiral cyclic subtrate, said substrate comprising a carbocycle or a heterocycle having a reactive center susceptible to nucleophilic attack by the nucleophile, in the presence of a chiral non-racemic catalyst to produce a product mixture comprising a stereomerically enriched product wherein the product mixture further comprises a catalyst residue, at least a portion of the catalyst residue is in a first oxidation state, and the catalyst residue in the first oxidation state is active in catalyzing degradation of the stereoisomerically enriched product, and (B) chemically or electochemically changing the oxidation state of the catalyst residue from the first oxidation state to a second oxidation state, wherein catalyst residue in the second oxidation state is less active in catalyzing degradation of the stereoisomerically enriched product than is catalyst residue in the first oxidation state. The method reduces erosion of the chiral purity of the stereoisomerically enriched product and reduces the chemical transformation to side products of the stereoisomerically enriched product and co-product(s). The deactivated catalyst is recoverable and recyclable.

39 Claims, No Drawings

KINETIC RESOLUTION METHOD

This application claims the priority of provisional application No. 60/314,247 filed on Aug. 22, 2001.

FIELD OF THE INVENTION

This invention relates to a method for stereoselective chemical synthesis, more particularly to a method for stereoselective chemical synthesis by the kinetic resolution of racemic terminal epoxides.

BACKGROUND OF THE INVENTION

Kinetic resolution, more particularly, hydrolytic kinetic resolution ("HKR") of racemic terminal epoxides, offers efficient and practical commercial access to enantiomerically enriched epoxides and 1,2-diols. The HKR method is catalyzed by cobalt(III) complexes of chiral salen ligands which can be prepared from the corresponding Co(II) complexes or from the direct reaction of salen ligand and Co(II) salts under air or oxygen, see, e.g., U.S. Pat. No. 6,262,278 B1, issued Jul. 17, 2001 for "STEREOSELECTIVE RING OPENING REACTIONS" by Eric N. Jacobsen et. al. and Ready, J. M., Jacobsen, E. N., "Highly Active Oligomeric (salen)Co Catalysts for Asymmetric Epoxide Ring Opening Reactions," *J. AM. Chem. Soc.* 2001, 123, 2687–2688.

HKR catalyst residues may catalyze undesired reactions and degrade the desired reaction products. For example, Co(III) complexes have been found to catalyze the formation of glycidol from the HKR product 3-chloro-1,2-propanediol, Furrow, M. E., Schaus, S. E., Jacobsen, E. N. "Practical Access to Highly Enantioenriched C-3 Building Blocks via Hydrolytic Kinetic Resolution," *J. Org. Chem.* 1998, 63, 6776. Undesired side reactions serve to diminish the yield and the chiral and chemical purity of the products, thereby making the manufacture of products of high chiral purity less efficient and more expensive.

SUMMARY OF THE INVENTION

The present invention is directed to a method for stereoselective chemical synthesis, comprising: reacting a nucleophile and a chiral or prochiral cyclic substrate, said substrate comprising a carbocycle or a heterocycle having a reactive center susceptible to nucleophilic attack by the nucleophile, in the presence of a chiral non-racemic catalyst to produce a product mixture comprising a stereoisomerically enriched product, wherein the product mixture further comprises a catalyst residue, at least a portion of the catalyst residue is in a first oxidation state and the catalyst residue in the first oxidation state is active in catalyzing degradation of the stereoisomerically enriched product, and chemically or electrochemically changing the oxidation state of the catalyst residue from the first oxidation state to a second oxidation state, wherein catalyst residue in the second oxidation state is less active in catalyzing degradation of the stereoisomerically enriched product than is catalyst residue in the first oxidation state.

The method of the present invention reduces erosion of chiral purity and the chemical transformation to side products of the stereoisomerically enriched product and its corresponding co-product(s) after the HKR. Additionally, the deactivated catalyst is recoverable and recyclable, which leads to a lower cost of the HKR process in the manufacture of key chiral building blocks.

In a first preferred embodiment, the present invention is directed to a method for stereoselective chemical synthesis, comprising reacting a nucleophile and a chiral or prochiral substrate in the presence of a chiral, nonracemic Co(III) salen catalyst to produce a product mixture comprising a stereoisomerically enriched product, wherein the product mixture further comprises a Co(III) salen catalyst residue that is active in catalyzing degradation of the stereoisomerically enriched product, and contacting the product mixture with at least one reducing agent selected from L-ascorbic acid, hydroquinone, hydroquinone derivatives, catechol and catechol derivatives to reduce the Co(III) salen catalyst residue to a Co(II) salen catalyst residue that is less active than the Co(III) salen catalyst residue in catalyzing degradation of the stereoisomerically enriched product.

In a second preferred embodiment, the present invention is directed to a method for stereoselective chemical synthesis, comprising reacting a nucleophile and chiral or prochiral substrate in the presence of a chiral, nonracemic Co(III) salen catalyst to produce a product mixture comprising a stereoisomerically enriched product, wherein the product mixture further comprises a Co(II) salen catalyst residue that is active in catalyzing degradation of the stereoisomerically enriched product, and contacting the product mixture with at least one oxidizing agent selected from hydrogen peroxide, peracids, persulfates, perborates, perchlorates, oxygen and air to oxidize the Co(II) salen catalyst residue to a Co(III) salen residue in the presence of a complexing agent effective in stabilizing the Co(III) salen residue, wherein the stabilized Co(III) salen residue is less active than the Co(II) salen catalyst residue in catalyzing degradation of the stereoisomerically enriched product.

DETAILED DESCRIPTION OF INVENTION AND PREFERRED EMBODIMENTS

In a preferred embodiment, the step of reacting the nucleophile and cyclic substrate is conducted according to the stereoselective synthesis processes described in U.S. Pat. No. 6,262,278 B1, issued Jul. 17, 2001 for "STEREOSELECTIVE RING OPENING REACTIONS" by Eric N. Jacobsen et. al., the disclosure of which is hereby incorporated herein by reference, provided that the present disclosure shall control in the event of any inconsistencies between the resent disclosure and the '278 patent.

For convenience, certain terms used in this application are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions.

The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "leaving group" is recognized in the art and as used herein means a chemical moiety that is bonded to the electrophilic center of a substrate and that, in the event that a nucleophile attacks and forms a new bond with the substrate, is replaced by the nucleophile. Exemplary leaving groups include sulfonates, carboxylates, carbonates, carbamates, phosphates and halides.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of asymmetry and whose molecules are not mirror images of one another.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "reaction product" means a compound which results from the reaction of a nucleophile and a substrate. In general, the term "reaction product" will be used herein to refer to a stable, isolable compound, and not to unstable intermediates or transition states.

As used herein in reference to a ligand, the term "asymmetric" means that the ligand comprises chiral centers that are not related by a plane or point of symmetry and/or that the ligand comprises an axis of asymmetry due to, for example, restricted rotation, helicity, molecular knotting or chiral metal complexation.

As used herein in reference to a ligand, the term "tetradentate" means that the ligand comprises four Lewis base substituents, which may be selected from, for example, oxygen atoms, sulfur atoms, nitrogen containing substituents, such as amino, amido, or imino groups, phosphorus-containing substituents, such as phosphine or phosphonate groups, and arsenic-containing substituents, such as arsine groups.

As used herein in reference to a complex of a metal atom and a tetradentate ligand, the term "rectangular planar" refers to a geometric configuration in which, subject to some distortion, the Lewis basic atoms of the complex each lie in substantially the same plane and are in a substantially rectangular arrangement and the metal atom of the complex lies in substantially the same plane.

As used herein to a complex of a metal atom and a tetradentate ligand, the term "rectangular pyramidal" refers to a geometric configuration in which, subject to some distortion, the Lewis basic atoms of the complex each lie in substantially the same plane and are in a substantially rectangular arrangement and the metal atom of the complex lies above or below the plane.

The term "complex" as used herein means a coordination compound formed by the union of one or more electronically rich molecules or atoms capable of independent existence with one or more electronically poor molecules or atoms, each of which is also capable of independent existence.

The term "substrate" is intended to mean a chemical compound which can react with a nucleophile, or with a ring-expansion regent, according to the present invention, to yield at least one product having a stereogenic center.

The term "catalytic amount" is recognized in the art and means a substoichiometric amount of catalyst relative to a reactant. As used herein, a catalytic amount means from 0.0001 to 90 mole percent catalyst relative to a reactant, more preferably from 0.001 to 50 mole percent, still more preferably from 0.01 to 10 mole percent, and even more preferably from 0.1 to 5 mole percent catalyst to reactant.

A "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

An "enantioselective reaction" is a reaction that converts an achiral reactant to a chiral, nonracemic product that is enriched in one enantiomer. Enatioselectivity is generally quantified in terms of "enantiomeric excess" ("e.e."), defined as:

$$e.e. = \left[\frac{(A-B)}{(A+B)}\right] \times 100$$

where A and B are the amounts of enantiomers formed. An enantioselective reaction yields a product with an e.e. greater than zero. Preferred enantioselective reactions yield an e.e. greater than 20%, more preferably greater than 50%, even more preferably greater than 70% and most preferably greater than 80%.

As used herein in reference to a stereoisomerically enriched product, the term "degradation" means a decrease in the yield or the enantiomeric excess of the product.

A "diastereoselective reaction" converts a chiral reactant (which may be racemic or enantiomerically pure) to a product enriched in one diastereomer.

If a chiral reactant is racemic, in the presence of a chiral non-racemic reagent or catalyst, one reactant enantiomer may react more slowly than the other. This is termed a "kinetic resolution", wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A "regioselective reaction" is a reaction which occurs preferentially at one reactive center rather than another reactive center. For example, a regioselective reaction of an unsymmetrically substituted epoxide substrate would cause preferential reaction at one of the two epoxide ring carbons.

The term "non-racemic" with respect to the chiral catalyst, means a preparation of catalyst having greater than 50% of a desired stereoisomer, more preferably at least 75%. "Substantially non-racemic" refers to preparations of the catalyst which have greater than 90% e.e. for a desired stereoisomer of the catalyst, more preferably greater than 95% e.e.

For purposes of this invention, the chemical elements are identified in accordance with the Periodic Table of the Elements, CAS version, Handbook of Chemistry and Physics, 67$^{th}$ Ed., 1986–87, inside cover. Also for purposes of this invention, the term "hydrocarbon" is contemplated to include all permissible compounds having at lease one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "alkyl" refers to the radical of saturated aliphatic groups, including straight-chain alkyl groups, branched chain alkyl groups, cycloalkyl (alicyclic) groups, alkyl substituted cycloalkly groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer carbon atoms in its backbone. Likewise, preferred cycloalkyls have from 4 to 10 carbon atoms in their ring structure, and more preferably have 5, 6 or 7 carbons in the ring tructure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl, an alkoxyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple bond respectively.

As used herein, "nitro" means —$NO_2$, "halo" means —F, —Cl, —Br or —I, "hydroxyl" means —OH, "carboxyl" means —COOH, "aldehyde" means —C(O)H, and "thio" means —SH, wherein, in each case, R is H, alkyl or aryl, and the term "organometallic" refers to a metallic atom such as mercury, zinc, lead, magnesium or lithium) or a metalloid (such as silicon, arsenic or selenium) which is bonded directly to a carbon atom, such as a diphenylmethoylsilyl group.

Thus, the term "alkylamine" as used herein means an alkyl group, as defined above, having a substituted or unsubstituted amine attached hereto. In exemplary embodiments, an "amine" can be represented by he general formula:

wherein $R^1$ and $R^2$ each independently represent a hydrogen, an alkyl, an alkenyl, —$(CH_2)_m$—$R^3$—C(=O)-alkyl, —C(=O)-alkenyl, —C(=O)-alkynyl, —C(=O)—$(CH_2)_m R^3$, or $R^1$ and $R^2$ taken together with the N atom to which they are attached complete a heterocycle having from 4 to 8 atoms in the ring structure; $R^3$ represents an aryl, a cycloalkyl, a cycloalkenyl, a heterocycle or a polycycle; and m is zero or an integer in the range of 1 to 8.

"Amido" means a substituent group according to the general formula:

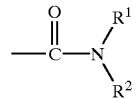

wherein $R^1$ and $R^2$ are as defined above.

"Imino" means a substituent group the general formula:

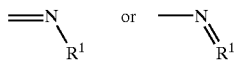

wherein $R^1$ is as described above, with the added proviso that $R^1$ cannot be H.

"Thioether" means a moiety represented by one of —S-alkyl, —S-alkenyl, —S-alkynyl, and —S—$(CH_2)_m R^3$, wherein m and $R^3$ are defined above.

The term "carbonyl" means —C(O)—. The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

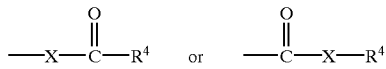

wherein X is absent or represents an oxygen or a sulfur, and $R^4$ represents a hydrogen, an alkyl, an alkenyl, or —$(CH_2)_m R^3$, where m and $R^3$ are as defined above. Where X is an oxygen, the formula represents an "ester". Where X is sulfur, the formula represents a "thioester". Where X is absent, and $R^4$ is not hydrogen, the above formula represents a "ketone" group. Where the oxygen atom of the above formula is replace by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O-alkyl, —O-alkenyl, —O-alkynyl, —O—$(CH_2)_m$—$R^3$ where m and $R^3$, are described above.

"Phosphoryl" can in general be represented by the formula:

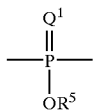

wherein $Q^1$ represented S or O, and $R^5$ represents hydrogen, a lower alkyl or an aryl. When used to substitute an alkyl, the phosphoryl group of the phosphorylalkyl can be represented by the general formula:

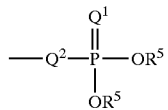

wherein $Q^1$ represented S or O, and each $R^5$ independently represents hydrogen, a lower alkyl or an aryl, $Q^2$ represents O, S or N.

As used herein the term "phosphino" includes —$PR_2$ and the term "phosphonato" means —$P(OR)_2$, wherein R is H, alkyl, aryl, heterocyclic or polycyclic.

In a preferred embodiment, the "silyl" moiety which may be substituted on the alkyl can be represented by the general formula:

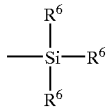

wherein each $R^6$ independently represents a hydrogen, an alkyl, an alkenyl, or —$(CH_2)_m$—$R^3$, wherein m and $R^3$ defined as above.

Exemplary "selenoethers" which may be substituted on the alkyl re selected from one of —Se—$(CH_2)_m$—$R^3$, wherein m and $R^3$ are defined as above.

The term "sulfonyl" as used herein means a $S(O)_2$ moiety bonded to two carbon atoms and the term "sulfonate" as used herein means a sulfonyl group, as defined above, attached to an alkoxy, aryloxy or hydroxy group. Thus, in a preferred embodiment, a sulfonate has the tructure:

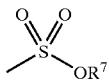

wherein $R^7$ is H, alkyl or aryl.

The term sulfate, as used herein, means a sulfonyl group, as defined above, attached to a hydroxy or alkoxy group. Thus, in a preferred embodiment, a sulfate has the structure:

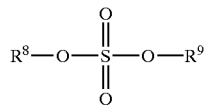

wherein $R^8$ and $R^9$ are independently absent, a hydrogen, an alkyl, or an aryl. Furthermore, $R^8$ and $R^9$ taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkyleneimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiopene, imidazole, oxazole, thiazole, triazole, pyrazole, pyridine, pyrazine, pyridazine and pyrimidine, and the like. Those aryl groups having heteroatoms in the ring positions may be substituted with such substituents as described above, for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R^3$, —$CF_3$, —CN, or the like, wherein m and $R^3$ are defined as above.

The term "heteroatom" as used herein means an atom of any element other than carbon or hydrogen. Preferred heteroatoms are nitrogen, oxygen, sulfur, phosphorus and selenium.

The terms "heterocycle" or "heterocyclic group" refer to 4 to 10-membered ring structures, more preferably 5 to 7-membered rings, which ring structures include one to four heteroatoms. Heterocyclic groups include pyrrolidine, oxolane, thiolane, imidazole, oxazole, piperidine, piperrazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, adehydes, esters, or —$(CH_2)_m R^3$, —$CF_3$, —CN, or the like, wherein m and $R^3$ are defined as above.

The term "carbocycle" refers generally to ring structures wherein the ring members are each carbon atoms.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, adehydes, esters, or —$(CH_2)_m R^3$, —$CF_3$, —CN, or the like, wherein m and $R^3$ are defined as above.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R^{10}$—$R^{11}$—$R^{12}$—, wherein $R^{11}$ is absent or represents an alkyl, an alkenyl, or an alkynyl, preferably $C_1$ to $C_{10}$, and $R^{10}$ and $R^{12}$ are each independently absent or represent an amine, an imine, an amide, a phosphoryl, a carbonyl, a silyl, an oxygen, a sulfonyl, a sulfur, a selenium, or an ester.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds, illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In one embodiment, the cyclic substrate comprises at least one compound according to formula (1):

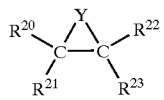

(1)

wherein:
$R^{20}$, $R^{21}$, $R^{22}$ and $R^{23}$ are each independently an organic or inorganic substituent which form a covalent bond with the carbon atom to which it is attached and which permit the formation of a stable ring structure including Y, and Y is O, S, $-NR^{24}$, $-C(R^{25})R^{26}$, or has the formula A-B-C, wherein $R^{24}$ is H, alkyl, carbonyl-substituted alkyl, carbonyl-substituted aryl or sulfonate, $R^{25}$ and $R^{26}$ are each independently an electron withdrawing group, A and C are each independently absent or ($C_1$-$C_5$)alkyl, O, S, carbonyl or $-NR^{24}$ and B is carbonyl, phosphoryl or sulfonyl.

In one preferred embodiment, $R^{20}$, $R^{21}$, $R^{22}$ and $R^{23}$ are each independently H, hydroxyl, halo, alkyl, alkenyl, alkynyl, amino, imino, amido, nitro, thio, phosphoryl, phosphonato, phosphino, carbonyl, carboxyl, silyl, sulfonyl, or a ketone, aldehyde, ester, thioether, selenoether, or $-(CH2)_n R^{27}$, wherein $R^{27}$ is aryl, cycloalkyl, cycloalkenyl or heterocyclyl and n is a number wherein $0 \leq n \leq 8$, or may alternatively, be fused with another one of the $R^{20}$, $R^{21}$, $R^{22}$ or $R^{23}$ substituents to form, together with the carbon atoms to which such substituents are attached, a carbocyclic or heterocyclic ring structure.

In another preferred embodiment, the substrate comprises a cyclic compound containing a electrophilic center and a leaving group, including, for example, epoxides, such as epichlorohydrin, aziridines, such as 1,2-propylene imine, episulfides, such as 1,2-propylene sulfide, cyclic carbonates, such as 1,2-propylene glycol cyclic carbonate, cyclic thiocarbonates, such as 1,2-propylene glycol cyclic thiocarbonate, cyclic phosphates, such as 1,2-propylene glycol cyclic phosphate, cyclic sulfates, such as 1,2-propylene glycol cyclic sulfate, cyclic sulfites, such as 1,2, propylene glycol cyclic sulfite, lactams, such as β-butyrolactam, thiolactams, such as β-butyrothiolactam, lactones, such as β-methyl-y-butyrolactone, thiolactones, such as β-methyl-y-butyrothiolactone, and sultones, such as 1,3-butyrosultone.

In general, any chemical compound having a reactive pair of electrons is suitable as the nucleophile of the present invention. Compounds that, under appropriate reaction conditions, are suitable for use as the nucleophile in the method of the present invention include, for example, hydride; uncharged compounds such as amines, mercaptans, and alcohols, including phenols; charged compounds such as alkoxides, phenoxides, thiolates; organic or inorganic anions, such as carbanions, azide, cyanide, thiocyanate, acetate, formate, chloroformate and bisulfite anions; organometallic reagents such as organocuprates, organozincs, organolithiums, Grignard reagents, enolates and acetylides.

In one preferred embodiment, the nucleophile comprises at least one compound selected from water, phenoxides, hydroxides, alkoxides, alcohols, thiols, thiolates, carboxylic acids and carboxylates, and, even more preferably, from water, phenols, particularly silyated phenols, and carboxylic acids.

In one embodiment, the chiral catalyst comprises a complex of an asymmetric tetradentate ligand with a first row transition metal atom, said complex having a rectangular planar or rectangular pyramidal geometry. Suitable tetradentate ligands are those derived from, for example, salens, porphyrins, crown ethers, azacrown ethers, cyclams or phthalocyanines. In a highly preferred embodiment, the tetradentate ligand is derived from a chiral salen or salen-like ligand.

In a preferred embodiment, the metal-asymmetric tetradentate ligand complex comprises at least one chiral metallosalenate according to the structural formula (2):

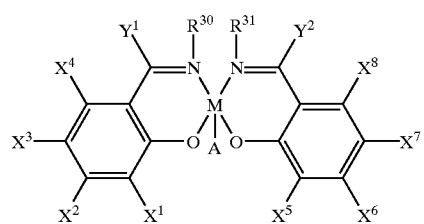

(2)

or structural formula (3):

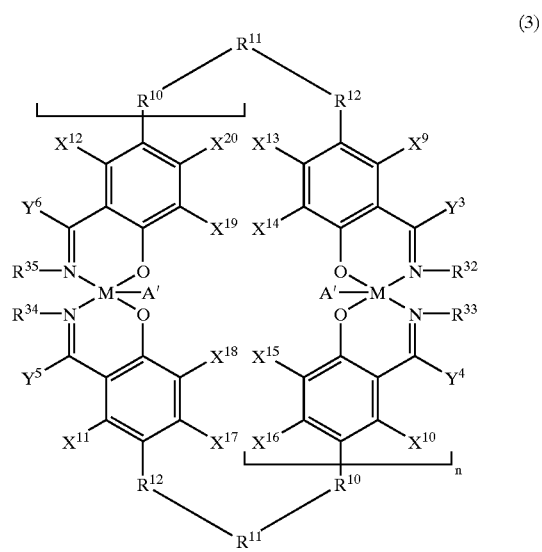

(3)

wherein:
$R^{30}$, $R^{31}$, $R^{32}$, $R^{33}$, $R^{34}$, $R^{35}$, $Y^1$, $Y^2$, $Y^3$, $Y^4$, $Y^5$, $Y^6$, $X^1$, $X^2$, $X^3$, $X^4$, $X^5$, $X^6$, $X^7$, $X^8$, $X^9$, $X^{10}$, $X^{11}$, $X^{12}$, $X^{14}$, $X^{15}$, $X^{16}$, $X^{17}$, $X^{19}$ and $X^{20}$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or $-(CH2)_{n'}$-$R^{36}$, wherein $R^{36}$ is aryl, cycloalkyl, cycloalkenyl or heterocyclyl or may alternatively, be fused with another one of the $R^{30}$, $R^{31}$, $R^{32}$, $R^{33}$, $R^{34}$, $R^{35}$, $Y^1$, $Y^2$, $Y^3$, $Y^4$, $Y^5$, $Y^6$, $X^1$, $X^2$, $X^3$, $X^4$, $X^5$, $X^6$, $X^7$, $X_8$, $X^9$, $X^{10}$, $X^{11}$, $X^{12}$, $X^{14}$, $X^{15}$, $X^{16}$, $X^{17}$, $X^{19}$ and $X^{20}$ substituents to form a carbocyclic or heterocyclic ring structure having from 4 to 8 carbon atoms in its ring, provided that, in each case, the substituents are selected to provide a compound having an asymmetric structure, and further provided that $R^{30}$ and $R^{31}$ are covalently bonded to each other to provide the compound of formula (2) as a tetradentate ligand, and that $R^{32}$ and $R^{33}$ are covalently bonded to each other and $R^{34}$ and $R^{35}$ are covalently bonded to each other to provide the compound of formula (3) as a tetradentate ligand, $R^{10}$, $R^{11}$ and $R^{12}$ are as described above, more preferably, $R^{10}$ and $R^{12}$ are each —OC(O)— or absent, and each $R^{11}$ is alkyl, more preferably, —$(CH_2)_{n''}$—, or —CH(Cl)$(CH_2)_m$CH(Cl)—, M is a first row transition metal atom, n, n', n" and m are each numbers, wherein $1 \leq n \leq 10$, $1 \leq n' \leq 15$, $1 \leq n'' \leq 13$, $1 \leq m \leq 9$ and A' is a counterion or nucleophile.

$R^{30}$ and $R^{31}$, $R^{32}$ and $R^{33}$, and $R^{34}$ and $R^{35}$ may, in each case, be directly covalently bonded to each other or may be indirectly covalently bonded to each other, such as, for example, via a bridging substituent.

As used herein, the terminology "first row transition metal atom" means an atom of an element listed in the first row of Groups 3–12 of the Periodic Table of elements, that is, Sc, Ti, V, Cr, Mn, Fe, Co, Ni, Cu, Zn.

In a highly preferred embodiment, the first row transition metal atom of the ligand metal atom complex is selected from Co, Cr and Mn.

In one preferred embodiment, the catalyst comprises at least one ligand-transition metal complex according to structure (2), wherein $R^{30}$ and $R^{31}$ are fused to form a 1,2-cyclohexylene group, Y', $Y^2$, $X^2$, $X^4$, $X^6$ and $X^8$ are each H, $X^1$, $X^3$, $X^5$ and $X^7$ are each t-butyl and M is Co.

In another preferred embodiment, the catalyst comprises at least one ligand-transition metal complex according to structure (3), wherein $R^{32}$ and $R^{33}$ are fused and $R^{34}$ and $R^{35}$ are fused to form respective 1,2-cyclohexylene groups, $Y^3$, $Y^4$, $Y^5$, $Y^6$, $X^9$, $X^{10}$, $X^{11}$, $X^{12}$, $X^{13}$, $X^{16}$, $X^{17}$, and $X^{20}$ are each H, $R^{10}$ and $R^{12}$ are each —OC(O)—, $R^{11}$ is —$(CH_2)_5$—, $X^{14}$, $X^{15}$, $X^{18}$ and $X^{19}$ are each t-butyl, each M is Co and n is 1–10.

In some cases, the catalyst is available in an oxidation state other than the first oxidation state and is relatively inactive in catalyzing the desired reaction of the nucleophile and substrate. In such cases, the catalyst must be activated, for example, by changing the oxidation state of the catalyst, prior to conducting reaction step of the stereoselective chemical synthesis of the present invention. For example, in some preferred embodiments of the present invention, a Co(II)-salen complex is activated, for example, by contacting the catalyst in dichloromethane with acetic acid ("HOAc") and air to form a Co(III)-salen complex.

In general, a mixture of the nucleophile, cyclic substrate, and a catalytic amount of chiral catalyst that is active in catalyzing the desired reaction of the substrate and nucleophile is maintained under conditions appropriate to allow the chiral catalyst to catalyze stereoselective pening of the cyclic substrate by the nucleophile at the electrophilic tom of the substrate.

Kinetic resolution of enantiomers occurs with chiral catalysis of a ring-opening reaction of a racemic substrate. In one embodiment, one enantiomer can be reacted with the nucleophile to form a desired reaction product and the other enantiomer recovered as unreacted substrate. Alternatively, the undesired enantiomer can be reacted with the nucleophile and the desired enantiomer recovered unreacted from the reaction mixture.

Catalyst residue is present in the product mixture. The catalyst residue may include catalyst residue that is identical to the catalyst used to catalyze the desired reaction of the nucleophile and substrate and may include catalyst residue that is a degraded form, e.g., a reduced or oxidized form, of the catalyst used to catalyze the desired reaction.

The presence of catalyst residue in the product mixture during product isolation may be detrimental to the chemical or chiral purity of the product by catalyzing undesired degradation of the stereoisomerically enriched product, such as, for example:

(i) in a hydrolytic kinetic resolution reaction, the catalyst in the first oxidation state may be active in catalyzing an undesired racemization, for example, it has been found that under typical HKR reaction conditions, Co(III) complexes catalyze the racemization of resolved epichlorohydrin via HCl addition to the epoxide to form achiral 1,3-dichoro-2-propanol and the low-enantioselective reverse reaction, (ii) in a reaction of a nucleophile, such as a phenol, with an epoxide that has a leaving group in the 3-position, the catalyst in the first oxidation state may be active in catalyzing undesired epoxide formation, for example:

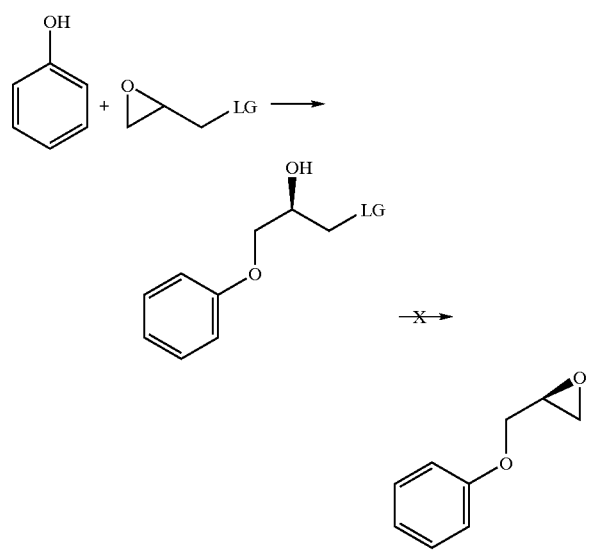

wherein LG=a leaving group, and (iii) in a reaction of an epoxide with an electron-deficient phenol, the catalyst in the first oxidation state may be active in catalyzing equilibration of regioisomers via an undesired Smiles Rearrangement, for example:

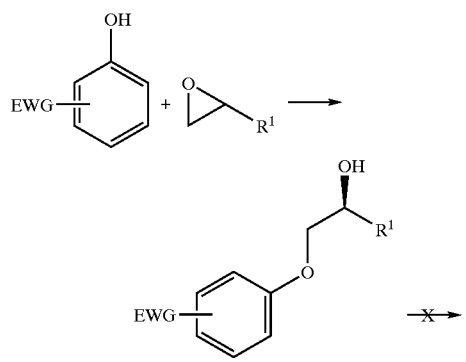

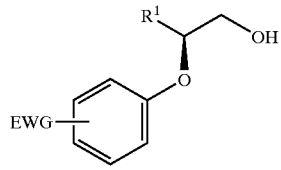

wherein EWG=an electron-withdrawing group.

In some embodiments, catalyst residue corresponding to the form of the catalyst used to catalyze the desired reaction may also be active in catalyzing less kinetically favored reactions that would degrade the desired product. For example, in the highly preferred embodiment of the HKR of epichlorohydrin, Co(III) salen catalyst is active in catalyzing the desired reaction of nucleophile and substrate and Co(III) salen catalyst residue is also active in catalyzing degradation of the stereoisomerically enriched product.

In other embodiments, catalyst residue corresponding to a degraded form of catalyst used to catalyze the desired reaction may be active in catalyzing reactions that degrade the desired product. For example, in the preferred embodiment of the HKR of styrene oxide, Co(III) salen catalyst is active in catalyzing the desired reaction of nucleophile and substrate and Co(II) salen catalyst residue generated during the reaction is active in catalyzing degradation of the stereoisomerically enriched product.

In either case, contact of the desired product with catalyst residue during isolation of the product can result in degradation of the stereoisomerically enriched product. Detriment to the chemical or chiral purity of the product that may arise due to the presence of catalyst residue during product isolation can be minimized by the process of the present invention.

Upon reaching stereoisomerically enriched product that exhibits a targeted degree of a stereoisomeric enrichment, such as for example, a targeted enantiomeric excess for the resolved product, the catalyst residue is treated, either chemically, electrochemically or a by combination thereof, to change the oxidation state of catalyst residue in a first oxidation state, in which the catalyst residue is active in catalyzing product degradation, from such first oxidation state, to a second oxidation state, in which the catalyst residue is relatively less active in catalyzing degradation of the product. In a preferred embodiment, the targeted degree of a stereoisomeric enrichment is production of a stereoisomerically enriched product that exhibits an enantiomeric excess of greater than or equal to 95%, more preferably, greater than or equal to 99%.

In one preferred embodiment, an organic or inorganic complexing agent effective in stabilizing the catalyst residue in the second oxidation state is added to the product mixture. The complexing agent may be any compound having a charged or uncharged component with a lone pair of electrons that is capable of binding with the transition metal complex and include, for example, ammonium hydroxide, amines, hydroxyamine, phosphines, sulfides, sulfoxides, amine N-oxides, amidines, quanidines, imidate esters phosphine oxides, carbon monoxide and cyanides.

In a preferred embodiment, the complexing agent comprises at least one amine according to the formula:

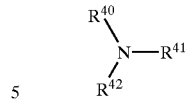

wherein $R^{40}$, $R^{41}$ and $R^{42}$ are each independently H, alkyl, alkenyl, alkynyl, aryl, heteroaryl, aralkyl, alkaryl or heterocyclic, or may, alternatively, be fused with another one of the $R^{40}$, $R^{41}$ and $R^{42}$ groups to form, together with the nitrogen atom to which they are attached, a heterocyclic 4 to 8-membered ring, any of which may be further substituted.

In a first embodiment, the oxidation state of catalyst residue is changed from the first oxidation state to the second oxidation state by reducing the catalyst residue.

In one preferred embodiment, the catalyst residue is chemically reduced by introducing an organic or inorganic reducing agent to the product mixture in an amount sufficient and under conditions appropriate to reduce any catalyst residue in the first oxidation state to catalyst residue in the second oxidation state. Suitable reducing agents may be any compound having sufficient reduction potential and reactivity to render it capable of reducing the active form of the ligand-transition metal atom complex, for example, a Co(III) complex or Cr(III) to a less reactive form of the complex, for example, a Co(II) complex or Cr(II) complex, under mild conditions and without adversely effecting the stereoisomerically enriched product. Typically, the reduction potential of the reagent used to reduce the active catalyst should be in the range of +0.1 to +0.6 v. This range is dependent upon the conditions of measurement as well as the reaction conditions under which the desired reaction occurs.

In another preferred embodiment, the reducing agent is selected from L-ascorbic acid, alcohols such as, for example, isopropanol, hydroquinone, and hydroquinone derivatives, such as for example, t-butylhydroquinone, catechol and catechol derivatives and mixtures thereof.

In a preferred embodiment, the reducing agent is contacted with the catalyst residue in an amount of from about 0.5 to about 10 mole equivalents of the reducing agent per mole of catalyst residue.

In general, the deactivation treatment step is conducted under mild conditions that will not adversely affect the product. In a preferred embodiment, the deactivation treatment step is conducted at a temperature of from about 5° C. to about 50° C., more preferably from about 15° C. to about 25° C.

In one preferred embodiment, Co(III)-salen complex is reduced by treatment with L-ascorbic acid. The treatment is conducted, for example, by contacting L-ascorbic acid with the Co(III)-salen complex. In a preferred embodiment, an amount of from about 0.5 to about 10 moles, more preferably from about 1 to about 2 moles, of L-ascorbic acid per mole of Co(III)-salen complex is contacted with the Co(III)-salen complex. In a preferred embodiment, the L-ascorbic acid is contacted with the Co(III)-salen complex at a temperature of about 5 to about 25° C. for a time period of about 30 to about 180 minutes. Preferably, the treatment is conducted by adding the L-ascorbic acid to the reaction mixture and agitating the mixture under the appropriate treatment conditions. The Co(III)-salen complex is observed to undergo reduction to Co(II)-salen complex by a color change and the precipitation of the Co(II)-salen complex. This treatment reduces, to the point of eliminating, erosion of the enantiomeric excess of resolved product, as well as to fully retarding the formation of side products.

In an alternative embodiment, the catalyst residue is electrochemically reduced by applying an electrical current to the product mixture, in an amount sufficient and under conditions appropriate to reduce any catalyst residue in the first oxidation state to the second oxidation state. As a further alternative, the catalyst residue may be reduced by a combination of the addition of a chemical reducing agent to the reaction mixture and the application of an electric current to the product mixture.

In a second embodiment, the oxidation state of the catalyst residue is changed from the first oxidation state to the second oxidation state by oxidizing the catalyst residue.

In a preferred embodiment, the catalyst residue is chemically oxidized by introducing an organic or inorganic oxidizing agent to the product mixture in an amount sufficient and under conditions appropriate to oxidize any catalyst residue in the first oxidation state to relatively less active catalyst residue in the second oxidation state. Suitable oxidizing agents may be any compound having sufficient oxidation potential and reactivity to render it capable of oxidizing the active form of the catalyst residue, for example, Co(II), Cr(II), to a less reactive form of the complex, for example, Co(III), Cr(III), under mild conditions and without adversely effecting the stereoisomerically enriched product, and include, for example, hydrogen peroxide, peracids, persulfates, perborates, perchlorates, oxygen and air.

In a preferred embodiment, Co(II)(salen) catalyst residue from a hydrolytic kinetic resolution of styrene oxide is oxidized from a first oxidation state to a second oxidation state in the presence of an organic or inorganic complexing agent that is capable of stabilizing the Co(II)(salen) catalyst residue in the second oxidation state. The resulting Co(III) (salen) catalyst residue-ammonium complex is less active than the Co(II)(salen) catalyst residue in catalyzing reactions that erode the e.e. of the enantiomerically enriched product.

In a highly preferred embodiment, the catalyst residue is oxidized with oxygen, preferably supplied in the form of an air stream, in the presence of ammonium hydroxide to form a Co(III)(salen) catalyst residue-ammonium complex.

In an alternative embodiment, the catalyst residue is electrochemically oxidized by applying an electrical current to the product mixture, in an amount sufficient and under conditions appropriate to oxidize any catalyst residue in the first oxidation state to the second oxidation state. As a further alternative, the catalyst residue may be oxidized by a combination of the addition of a chemical oxidizing agent to the reaction mixture and the application of an electric current to the product mixture.

In typical large HKR reactions, it has not been possible to recycle the HKR catalyst. Following treatment according to the method of the present invention to deactivate the catalyst, the product can be purified and the deactivated catalyst can be recovered from the product mixture by conventional techniques, such as for example, distillation, filtration, extraction. Once recovered, the deactivated catalyst can be reactivated, that is, by changing the oxidation state of the recovered catalyst to increase the catalytic activity of the catalyst.

In the preferred embodiment of HKR of an epoxide using a Co(III)-salen complex, the resolved epoxide can typically be separated from the product mixture by distillation and the reduced activity Co(II)-salen complex can be recovered from the diol co-product by the addition of water and either filtration of the insoluble complex or extraction into an organic solvent. This recovered catalyst can be reactivated by oxidation to Co(III) by treatment with carboxylic or sulfonic acids in air or oxygen as previously described with no loss of reactivity or selectivity.

The treatment process allows the HKR to be performed, including the initial activation of the metal-salen complex, with or without an organic co-solvent.

EXAMPLE 1

Racemic epichlorohydrin was resolved to (R)-epichlorohydrin according to the following reaction scheme:

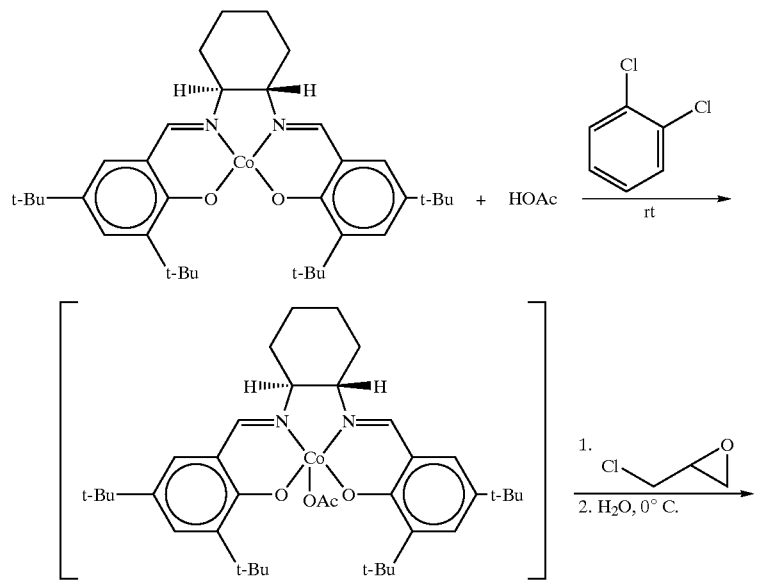

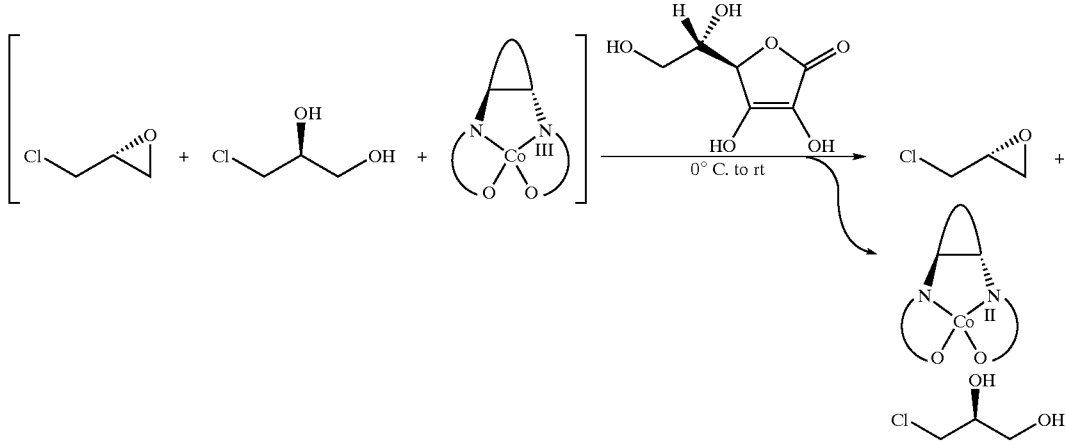

(S,S)—Co(II)-salen complex (60.06 g) was mixed with o-dichlorobenzene (304 g) and activated by adding acetic acid (11.98 g, 2 equiv.) to the mixture.

Active catalyst solution (369 g) was introduced to a 2.5 liter jacketed reaction vessel and racemic epichlorohydrin (1740 g) was then added to the vessel. Water (258 g) was added to the reaction vessel at a constant flow rate over 3 hours and hydrolytic kinetic resolution of the epichlorohydrin was carried out at 5° C. The mixture was stirred until the product mixture exhibited an enantiomeric excess of greater than 99%, that is, for an additional period of about 1.5 hours. The product mixture contained 35 wt % (R)-epichlorohydrin (47% theoretical yield), 0.2 wt % (S)-epichlorohydrin, 3.4 wt % water, 46 wt % CPD, 0.8 wt % glycidol, 0.9 wt % dichloropropanol and 13.6 wt % o-dichlorobenzene.

Part (1130 g) of the product mixture was removed from the reaction vessel. L-ascorbic acid (1 mole % catalyst, based on epoxide) was added to the remaining product and stirred for 30 minutes at room temperature.

The removed product mixture that had not been treated with L-ascorbic acid was, after about 2 hours (by which time the (R)-epichlorohydrin product content had already deteriorated from 35 wt % to 33.5 wt %), was subjected to short path distillation in a wiped film evaporator (Luwa) at a flow rate of 630 mL/h and a residence time of 20 seconds at a jacket temperature of 55° C. and a pressure of 27 millibars in order to isolate the (R)-epichlorohydrin product.

An organic phase (257.7 g), an aqueous phase (23.3 g) and tarry residue (510.5 g) having the respective relative compositions set forth below (in wt %) in TABLE I (as determined by gas chromatographic analysis and wherein (R)-epi=(R)-epichlorohydrin, CPD=3-chloro-1,2-propanediol, DCP=1,3-dichloro-3-propanol and o-DCB=ortho-dichlorobenzene) were collected in the distillation process.

TABLE I

Results for (R)-epichlorohydrin product, without L-Ascorbic acid treatment, isolated by short path distillation in wiped film evaporator

|  | (R)-epi | CPD | Glycidol | DCP | o-DCB |
|---|---|---|---|---|---|
| Organic Phase | 84% | 0.1% | — | 0.15% | 16.2% |
| Aqueous Phase | 5.6% | 3.51% | 1.32% | 0.06% | — |
| Residue | 1.8% | 65.5% | 2.51% | 12.71% | 12.4% |

(R)-epichlorohydrin product (216 g, 37% theoretical yield) was isolated from the organic phase.

Twenty-four hours after ascorbic acid treatment, a viscous mixture remained in the reaction vessel. DCB (200 mL) was added to the reaction vessel in order to reduce the viscosity of the viscous mixture. The mixture (1080 g) is then vacuum distilled over five hours at a pressure of 25 millibars and a pot temperature of 50° C. to produce an organic phase (278 g), an aqueous phase 25 g) and residue (710.8 g) having the respective relative compositions (in wt %) given below in TABLE II (as determined by gas chromatographic analysis and wherein (R)-epi=(R)-epichlorhydrin, CPD 3-chloro-1,2-propanediol, DCP=1,3-dichloro-3-propanol and o-DCB=ortho-dichlorobenzene).

TABLE II

Results for (R)-epichlorohydrin product, with L-ascorbic acid treatment, isolated by vacuum distillation from reaction vessel

|  | (R)-epi | CPD | Glycidol | DCP | o-DCB |
|---|---|---|---|---|---|
| Organic Phase | 88.9% | —% | — | —% | 10.5% |
| Residue | 6.9% | 70.8% | 0.4% | 0.8% | 23.5 |

The organic phase consisted of a binary (R)-epichlorohydrin/o-DCB mixture and the residue contained a very low level of decomposition products, i.e., glycidol and DCP, compared to the residue from the short path distillation. The results show the increased stability of the L-ascorbic acid treated product, particularly in view of the very mild short path distillation conditions used to fractionate the non-treated product mixture and the more severe vacuum distillation conditions used to fractionate the L-ascorbic acid-treated product mixture.

(R)-epichlorohydrin product (247g, 38.5% theoretical yield) was isolated from the organic phase. In view of the relatively large amount of (R)-epichlorohydrin in the distillation residue, it is apparent that more (R)-epichlorohydrin product (potentially, a total yield of up to about 46% of the possible 50% theoretical yield) could have been recovered by continuing the distillation at higher temperature and/or lower pressure.

In a typical Hydrolytic Kinetic Resolution (HKR) of epichlorohydrin, the active Co(III) complex catalyzes the erosion of enantiomeric excess of the resolved epoxide and diol product (3-chloro-1,2-propanediol) and the chemical degradation of the mixture by conversion to side products. The treatment of the resolved HKR mixture with ascorbic acid leads to the reduction of Co(III)-salen catalyst to the less-soluble Co(II)-salen complex, resulting in a heterogeneous mixture which is thermally stable and shows no erosion of e.e. or degradation to side products. Furthermore, the Co(II) complex can be recovered by filtration or extraction and recycled multiple times with no decrease in reactivity or selectivity.

EXAMPLE 2

Racemic epichlorohydrin was resolved to (S)-epichlorohydrin. (R,R)—Co(II)-salen complex (3 g; 4.97 mmol; 0.5 mol %) was charged to a 125-mL, 3-neck, jacketed round bottom flask equipped with a mechanical stirrer.

$CH_2Cl_2$ (12 mL, 4 volumes) was then charged to the vessel. Glacial acetic acid (0.57 mL; 9.96 mmol; 1.0 mol %; 2 equiv. to catalyst) was then charged to the vessel in one portion. The resulting mixture was stirred in open atmosphere for 0.5 h, which resulted in a dark mixture. The reaction mixture was visually inspected to confirm absence of bright red solid and presence of dark brown solution. The flask was then equipped with a cold (dry ice/IPA) finger trap. $CH_2Cl_2$ was removed under house vacuum to dryness at ambient temperature and the $CH_2Cl_2$ distillate was discharged to waste.

Racemic epichlorohydrin (78 mL; 1.0 mol) was then charged to the vessel. The reaction mixture was stirred and the temperature of the reaction mixture was adjusted to 5° C. with a recirculating water/ethylene glycol chiller. Water (11.7 mL, 0.65 mol, 0.65 equiv. to Epi) was then charged to vessel in ca 1 mL/5 min portions via syringe. An 8° C. exotherm was observed for the reaction. The reaction mixture was then stirred at 5° C. for 4.5 hours. The reaction mixture was sampled for completion via pipet (Chiral GC assay NLT 99.0% e.e.). It took 4.0 h to reach 99% e.e. (3 h after all the water was charged).

L-ascorbic acid (1.75 g; 9.94 mmol; 2 equiv. to catalyst) was then added to the cold mixture and stirred overnight while warming to ambient temperature. $H_2O$ (25 mL) was then added to the vessel and the red Co(II) salen was collected by filtration through qualitative paper. The filter cake was then washed with additional $H_2O$ (25 mL) and then dried overnight in a vacuum oven at 55 to 60° C. under house vacuum. 1.9 g (3 g theory) of red Co(II) salen catalyst was recovered.

The filtrate was transferred to a 250 mL round bottom flask and equipped for short-path distillation and apply vacuum at 50 torr and gradually decrease pressure to 20 torr. The filtrate had a dark red color, indicative of dissolved catalyst. The filtrate was then distilled at 20° C. and 20 torr and the contents of the still pot were allowed to cool to ambient temperature. A distillate was collected at 20° C. and 20 torr to give 32.85 g of (S)-Epichlorohydrin (>99% e.e., >99% chemical purity, GC, % area) was obtained with observed water as co-distillate, resulting in two immiscible liquids.

EXAMPLE 3

Racemic epichlorohydrin was resolved using (R,R)—Co (II)-salen complex in a process analogous to that set forth above in Example 1 to obtain >99% e.e. of resolved (S)-epichlorohydrin and the product mixture was treated with several additives, each a potential reducing agent. The reaction mixture was subsequently divided into eight portions (12 g each) in separate scintillation vials, each equipped with a magnetic stir bar. The effect of catalyst deactivation and stabilization of resolved (S)-epichlorohydrin were analyzed with respect to time and temperature. Two of the eight vials were used as controls, to which nothing was added and the remaining six (6) portions were separately treated with 5.51 mmol (approximately 2 equivalents to the catalyst present) of various additives.

The composition of the product mixture was monitored over time by gas chromatographic analysis using the ortho-dichlorobenzene co-solvent as an internal standard. Results are given below in TABLES III and IV, which set forth, in each case, the additive, the amount of additive used, the time elapsed from addition of the additive to the analysis, the temperature at which the sample was maintained during the elapsed time (wherein "RT" means room temperature) and the sample composition (wherein e.e.=enantiomeric excess, (R)-epi=(R)-epichlorhydrin, CPD=3-chloro-1,2-propanediol, DCP=1,3-dichloro-3-propanol and o-DCB ortho-dichlorobenzene).

TABLE III

| Additive | Time (hr) | T (° C.) | e.e. (%) | EPI (%) | Glycidol (%) | DCP (%) | CPD (%) | o-DCB (%) |
|---|---|---|---|---|---|---|---|---|
| No additive | 4 | RT | 99.3 | 24.0 | 1.5 | 2.8 | 24.0 | 46.6 |
|  | 68 | RT | 71.5 | 14.5 | 3.6 | 10.9 | 17.3 | 49.3 |
| $HCO_2NH_4$ (0.32 g) | 4 | RT | 99.8 | 26.3 | 0.56 | 1.1 | 24.7 | 46.3 |
|  | 68 | RT | 99.5 | 25.1 | 0.96 | 1.8 | 24.2 | 46.5 |
|  | 18 | 60 | 1.3 | 7.4 | 3.6 | 14.0 | 15.3 | 52.0 |

TABLE IV

| Additive | Time (hr) | T (° C.) | e.e. (%) | EPI (%) | Glycidol (%) | DCP (%) | CPD (%) | o-DCB (%) |
|---|---|---|---|---|---|---|---|---|
| No additive | 0 | 4.9 | 99.5 | 27.9 | 0.54 | 0.71 | 24.7 | 45.1 |
|  | 4 | RT | 99.3 | 25.0 | 1.3 | 2.4 | 24.5 | 45.6 |
|  | 71 | RT | 72.4 | 15.8 | 3.6 | 11.2 | 16.9 | 48.5 |
| $NaBH_4$ (0.19 g) | 4 | RT | 99.6 | 27.5 | 1.4 | 1.0 | 20.7 | 47.8 |
|  | 71 | RT | 94.5 | 14.9 | 0.75 | 6.6 | 14.2 | 53.2 |
| Formic acid (0.19 mL) | 4 | RT | 99.6 | 26.2 | 0.41 | 1.0 | 25.6 | 45.4 |
|  | 71 | RT | 99.5 | 22.9 | 0.62 | 1.5 | 23.9 | 46.1 |
|  | 15 | 66 | −12.4 | 8.7 | 5.3 | 13.4 | 17.2 | 48.9 |
|  | 24 | 66 | −0.03 | 7.9 | 4.7 | 13.5 | 17.9 | 48.9 |
| Hydroquinone (0.56 g) | 4 | RT | 99.6 | 25.5 | 0.49 | 0.92 | 23.5 | 42.9 |
|  | 71 | RT | 99.6 | 26.4 | 0.52 | 1.1 | 22.4 | 43.8 |
|  | 15 | 66 | 99.1 | 24.0 | 1.5 | 2.7 | 21.3 | 44.8 |
|  | 24 | 66 | 98.5 | 22.3 | 2.1 | 3.7 | 21.8 | 44.5 |
| L-Ascorbic acid (0.90 g) | 4 | RT | 99.6 | 27.3 | 0.45 | 1.0 | 25.1 | 45.6 |
|  | 71 | RT | 99.6 | 27.0 | 0.44 | 1.1 | 24.9 | 45.3 |
|  | 15 | 66 | 99.6 | 24.1 | 0.24 | 1.1 | 23.8 | 46.8 |
|  | 24 | 66 | 99.6 | 22.7 | 0.20 | 1.2 | 23.8 | 47.4 |
| $Mn(OAc)_2 \cdot 4H_2O$ (1.25 g) | 4 | RT | 99.7 | 26.5 | 0.40 | 1.1 | 22.1 | 47.4 |
|  | 71 | RT | 99.7 | 23.5 | 0.35 | 1.6 | 23.2 | 46.2 |
|  | 15 | 66 | 39.1 | 6.3 | 1.6 | 13.8 | 14.1 | 51.7 |
|  | 24 | 66 | 7.7 | 2.9 | 0.72 | 16.4 | 13.1 | 53.4 |

Treatment with each of the additives provided improved stability at room temperature, compared to the control. Treatment with L-ascorbic acid or hydroquinone provided improved stability at elevated temperature compared to the control, with L-ascorbic acid providing better stability compared to hydroquinone.

EXAMPLE 4

Racemic styrene oxide was resolved to (S)-styrene oxide and (R)-styrene glycol using (S,S)—Co(salen) according to the following reaction scheme:

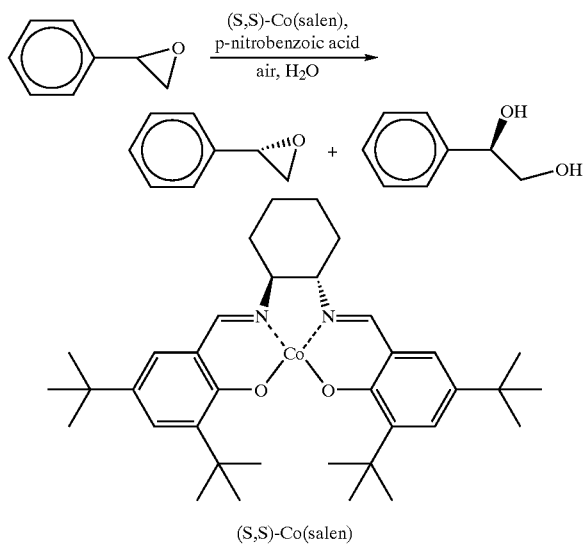

(S,S)-Co(salen)

A 500-mL flask, equipped with a temperature probe, a mechanical stirrer, a vacuum adapter, and a dip tube, was charged with (S,S)—Co(salen) (5.51 g, 0.0083 mol, 0.500 mol %), styrene oxide (200.0 g, 1.66 mol, 100 mol %), and water (59.8 g, 3.32 mol, 200 mol %). A slight vacuum was applied to the flask to draw air into the reaction mixture through the dip tube (subsurface), and agitation was initiated. The flask was placed in a water bath and p-nitrobenzoic acid (2.83 g, 0.0166 mol, 1.00 mol %) was added in one portion. After stirring overnight at room temperature, the reaction was deemed complete by HPLC. The reaction mixture was a brown solution with suspended orange solids. Ammonium hydroxide (4.15 g, 4.63 mL, 28% $NH_3$, 0.0332 mol, 2.00 mol %) was added and the reaction mixture was stirred at room temperature with continued air flow for 1 h. A dark brown solution was obtained. Air flow through the reaction mixture was stopped, and the reaction mixture was washed with water (2×200 mL). The organic layer was fractionally distilled to give (S)-styrene oxide (67.86 g, 67.9% yield, 99.6% e.e.). The aqueous layer was treated with activated carbon and warmed to a gentle boil. After cooling and filtration, the aqueous layer was concentrated to give (R)-styrene glycol (95.25 g, 95.3% yield, 93.9% e.e.).

EXAMPLE 5

The stability of (S)-styrene oxide was tested under several different conditions. The following mixtures were prepared:

Example 7A consisted of (S)-styrene oxide,

Example 7B consisted of 91 pbw (S)-styrene oxide, 6.4 pbw Co(III) salen catalyst, 1.2 pbw acetic acid and 1.6 pbw sodium acetate, Example 7C consisted of 91.3 pbw (S)-styrene oxide, 6.4 pbw Co(III) salen catalyst, 1.2 pbw acetic acid and 1.1 pbw aqueous ammonia.

The mixtures of Examples 7B–7C were heated to and maintained at 70° C. for a time period of 48 hours. The relative amounts of (R)— and (S)—styrene oxide present in each mixture was monitored over the time period and used to calculate percent enantiomeric excess of the (S)— enantiomer. TABLE V below shows the enantiomeric excess for each of the mixtures of Examples 7A–7C over the time period.

TABLE V

Enantiomeric Excess (%) for (S)-Styrene Oxide Mixtures Over Time

| | 1 hour | 2 hours | 21 hours | 30 hours | 48 hours |
|---|---|---|---|---|---|
| EX 7A | 99.8 | 99.9 | 99.8 | 99.8 | 99.8 |
| Ex 7B | 99.7 | 99.4 | 95.4 | 92.7 | 91.1 |
| Ex 7C | 99.6 | 99.7 | 99.0 | 98.4 | 98.6 |

What is claim is:

1. A method for stereoselective chemical synthesis, comprising:

reacting a nucleophile and a chiral or prochiral cyclic substrate, said substrate comprising a carbocycle or a heterocycle having a reactive center susceptible to nucleophilic attack by the nucleophile, in the presence of a chiral non-racemic catalyst to produce a product mixture comprising a stereoisomerically enriched product, wherein the product mixture further comprises a catalyst residue, at least a portion of the catalyst residue is in a first oxidation state and the catalyst residue in the first oxidation state is active in catalyzing degradation of the stereoisomerically enriched product, and chemically or electrochemically changing the oxidation state of the catalyst residue from the first oxidation state to a second oxidation state, wherein catalyst residue in the second oxidation state is less active in catalyzing degradation of the stereoisomerically enriched product than is catalyst residue in the first oxidation state.

2. The method of claim 1, wherein the cyclic substrate comprises at least one compound according to formula (1):

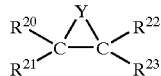

(1)

wherein:

$R^{20}$, $R^{21}$, $R^{22}$ and $R^{23}$ are each independently an organic or inorganic substituent which form a covalent bond with the carbon atom to which it is attached and which permit the formation of a stable ring structure including Y, and Y is O, S, —$NR^{24}$, —$C(R^{25})R^{26}$, or has the formula —A—B—C, wherein $R^{24}$ is H, alkyl, carbonyl-substituted alkyl, carbonyl-substituted aryl or sulfonate, $R^{25}$ and $R^{26}$ are each independently an electron withdrawing group, A and C are each independently absent or ($C_1$–$C_5$)alkyl, O, S, carbonyl or —$NR^{24}$, and B is carbonyl, phosphoryl, or sulfonyl.

3. The method of claim 2, wherein $R^{20}$, $R^{21}$, $R^{22}$ and $R^{23}$ are each independently H, hydroxyl, halo, alkyl, alkenyl, alkynyl, amino, imino, amido, nitro, thio, phosphoryl, phosphonato, phosphino, carbonyl, carboxyl, silyl, sulfonyl, or a ketone, aldehyde, ester, thioether, selenoether, or —$(CH2)_nR^{27}$ wherein $R^{27}$ is aryl, cycloalkyl, cycloalkenyl or heterocyclyl and n is a number wherein $0 \leq n \leq 8$, or may alternatively, be fused with another one of the $R^{20}$, $R^{21}$, $R^{22}$ or $R^{23}$ substituents to form, together with the carbon atoms to which such substituents are attached, a carbocyclic or heterocyclic ring structure.

4. The method of claim 1, wherein the cyclic substrate comprises at least one compound selected from epoxides, aziridines, episulfides, cyclic carbonates, cyclic thiocarbonates, cyclic phosphates, cyclic sulfates, cyclic sulfites, lactams, thiolactams, lactones, thiolactones, and sultones.

5. The method of claim 1, wherein the nucleophile comprises at least one compound selected from water, phenoxides, hydroxides, alkoxides, alcohols, thiols, thiolates, carboxylic acids, and carboxylates.

6. The method of claim 1, wherein the nucleophile comprises at least one compound selected from water, phenols, and carboxylic acids.

7. The method of claim 1, wherein the catalyst comprises a complex of an asymmetric tetradentate ligand with a first row transition metal atom and exhibits a rectangular planar or rectangular pyramidal geometry.

8. The method of claim 1, wherein the catalyst comprises at least one chiral metallosalenate according to the structural formula (2):

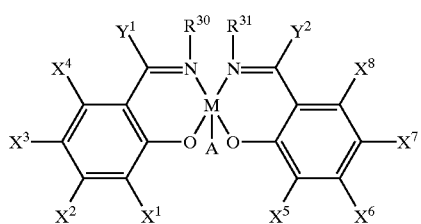

(2)

or structural formula (3):

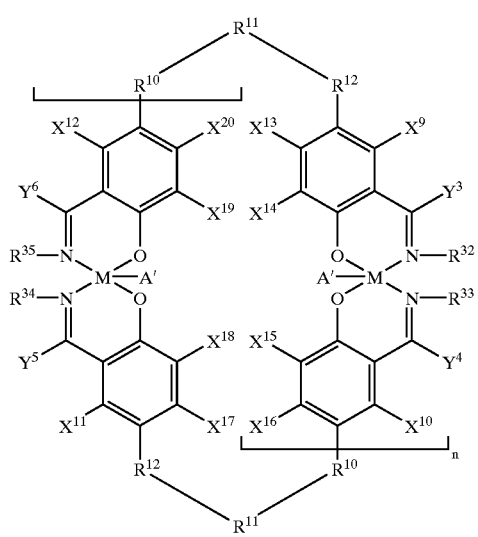

(3)

wherein:
$R^{30}$, $R^{31}$, $R^{32}$, $R^{33}$, $R^{34}$, $R^{35}$, $Y^1$, $Y^2$, $Y^3$, $Y^4$, $Y^5$, $Y^6$, $X^1$, $X^2$, $X^3$, $X^4$, $X^5$, $X^6$, $X^7$, $X^8$, $X^9$, $X^{10}$, $X^{11}$, $X^{12}$, $X^{14}$, $X^{15}$, $X^{16}$, $X^{17}$, $X^{19}$ and $X^{20}$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester, or —(CH2)$_n$— $R^{36}$, wherein $R^{36}$ is aryl, cycloalkyl, cycloalkenyl or heterocyclyl or may alternatively, be fused with another one of the $R^{30}$, $R^{31}$, $R^{32}$, $R^{33}$, $R^{34}$, $R^{35}$, $Y^1$, $Y^2$, $Y^3$, $Y^4$, $Y^5$, $Y^6$, $X^1$, $X^2$, $X^3$, $X^4$, $X^5$, $X^6$, $X^7$, $X^8$, $X^9$, $X^{10}$, $X^{11}$, $X^{12}$, $X^{14}$, $X^{15}$, $X^{16}$, $X_{17}$, $X^{19}$ and $X^{20}$ substituents to form a carbocyclic or heterocyclic ring structure having from 4 to 8 carbon atoms in its ring, provided that, in each case, the substituents are selected to provide a compound having an asymmetric structure, and further provided that $R^{30}$ and $R^{31}$ are covalently bonded to each other to provide the compound of formula (2) as a tetradentate ligand, and that $R^{32}$ and $R^{33}$ are covalently bonded to each other and $R^{34}$ and $R^{35}$ are covalently bonded to each other to provide the compound of formula (3) as a tetradentate ligand, $R^{10}$, $R^{11}$ and $R^{12}$ are as described above, more preferably, $R^{10}$ and $R^{12}$ are each —OC(O)— or absent, and each $R^{11}$ is alkyl, more preferably, —(CH2)$_{n''}$—, or —CH(Cl)(CH$_2$)$_m$CH(Cl)—, M is a first row transition metal atom, n, n', n'' and m are each numbers, wherein $1 \leq n \leq 10$, $1 \leq n' \leq 15$, $1 \leq n'' \leq 13$, $1 \leq m \leq 9$ and A' is a counterion or nucleophile.

9. The method of claim 8, wherein $R^{10}$ and $R^{12}$ are each —OC(O)— or absent, and each $R^{11}$ is —(CH2)$_{n'}$—, or —CH(Cl)(CH$_2$)$_m$CH(Cl)—.

10. The method of claim 8, wherein the catalyst comprises at least one complex according to structure (2).

11. The method of claim 10, wherein $R^{30}$ and $R^{31}$ are fused to form a 1,2-20 cyclohexylene group, $Y^1$, $Y^2$, $X^2$, $X^4$, $X^6$ and $X^8$ are each H, $X^1$, $X^3$, $X^5$, and $X^7$ are each t-butyl and M is Co.

12. The method of claim 8, wherein the catalyst comprises at least one complex according to structure (3).

13. The method of claim 12, wherein $R^{32}$ and $R^{33}$ are fused and $R^{34}$ and $R^{35}$ are fused to form respective 1,2-cylcohexylene groups, $Y^3$, $Y^4$, $Y^5$, $Y^6$, $X^9$, $X^{10}$, $X^{11}$, $X^{12}$, $X^{13}$, $X^{16}$, $X^{17}$, and $X^{20}$ are each H, $R^{10}$ and $R^{12}$ are each —OC(O)—, $R^{11}$ is —(CH$_2$)$_5$—, $X^{14}$, $X^{15}$, $X^{18}$, and $X^{19}$ are each t-butyl, each M is Co and n is 1–10.

14. The method of claim 1, wherein the stereoselective synthesis comprises hydrolytic kinetic resolution of a mixture of enantiomers or diastereomers and wherein the catalyst in the first oxidation state is active in catalyzing undesired racemization of the resolved product.

15. The method of claim 1, wherein the nucleophile comprises a phenol, the cyclic substrate comprises an epoxide having a leaving group in the 3-position and wherein the catalyst in the first oxidation state is active in catalyzing undesired epoxide formation.

16. The method of claim 1, wherein the nucleophile comprises an electron-deficient phenol, the cyclic substrate comprises an epoxide and wherein the catalyst in the first oxidation state is active in catalyzing equilibration of regioisomers via an undesired Smiles Rearrangement.

17. The method of claim 1, wherein the oxidation state of the catalyst residue is changed by reducing the catalyst residue.

18. The method of claim 17, wherein a Co(III) or Cr(III) catalyst residue is reduced to a Co(II) or Cr(II) catalyst residue.

19. The method of claim 17, wherein the catalyst residue is reduced by contacting the catalyst residue with at least one reducing agent selected from L-ascorbic acid, an alcohol hydroquinone, hydroquinone derivatives, catechol, catechol derivatives, and mixtures thereof.

20. The method of claim 1, wherein the oxidation state of the catalyst residue is changed by oxidizing the catalyst residue.

21. The method of claim 20, wherein a Co(II) or Cr(II) catalyst residue is oxidized to a Co(III) or Cr(III) catalyst residue.

22. The method of claim 20, wherein the catalyst residue is oxidized by contacting the catalyst residue with at least one oxidizing agent selected from hydrogen peroxide, peracids, persulfates, perborates, perchlorates, oxygen, and air.

23. The method of claim 1, further comprising adding to the product mixture a complexing agent effective to stabilize the catalyst residue in the second oxidation state.

24. The method of claim 23, wherein the complexing agent comprises at least one compound selected from ammonium hydroxide, amines, hydroxyamine, phosphines, sulfides, sulfoxides, amine N-oxides, amidines, quanidines, imidate esters, phosphine oxides, carbon monoxide, and cyanides.

25. The method of claim 23, wherein the complexing agent comprises at least one amine according to the formula:

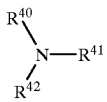

wherein $R^{40}$, $R^{41}$ and $R^{42}$ are each independently H, alkyl, alkenyl, alkynyl, aryl, heteroaryl aralkyl, alkaryl, or heterocyclic, or may, alternatively, be fused with another one of the $R^{40}$, $R^{41}$ and $R^{42}$ groups to form, together with the nitrogen atom to which they are attached, a heterocyclic 4 to 8-membered ring, any of which may be further substituted.

26. The method of claim 1, further comprising recovering and recycling the catalyst residue.

27. A method for stereoselective chemical synthesis, comprising:
   reacting a nucleophile and a chiral or prochiral substrate in the presence of a chiral, nonracemic Co(III) salen catalyst to produce a product mixture comprising a stereoisomerically enriched product, wherein the product mixture further comprises a Co(III) salen catalyst residue that is active in catalyzing degradation of the stereoisomerically enriched product, and
   contacting the product mixture with at least one reducing agent selected from L-ascorbic acid, hydroquinone, hydroquinone derivatives, catechol and catechol derivatives to reduce the Co(III) salen catalyst residue to a Co(II) salen catalyst residue that is less active than the Co(III) salen catalyst residue in catalyzing degradation of the stereoisomerically enriched product.

28. The method of claim 27, wherein the nucleophile comprises water.

29. The method of claim 27, wherein the substrate comprises a mixture of epoxide enantiomers.

30. The method of claim 27, wherein the substrate comprises a mixture of epichlorohydrin enantiomers.

31. The method of claim 27, wherein the reducing agent comprises L-ascorbic acid.

32. The method of claim 27, further comprising recovering the Co(II) salen catalyst residue and oxidizing the recovered catalyst residue to form Co(III) salen catalyst.

33. A method for stereoselective chemical synthesis, comprising:
   reacting water and a mixture of (R)-epichlorhydrin and (S)-epichlorhydrin enantiomers in the presence of a chiral non-racemic Co(III) salen catalyst to produce a product mixture that is stereoisomerically enriched in one of the epichlorohydrin enantiomers, wherein the product mixture further comprises a Co(III) salen catalyst residue, and
   contacting the product mixture with L-ascorbic acid to reduce the Co(II) salen catalyst residue to a Co(II) salen catalyst residue.

34. A method for stereoselective chemical synthesis, comprising:
   reacting a nucleophile and chiral or prochiral substrate in the presence of a chiral, nonracemic Co(III) salen catalyst to produce a product mixture comprising a stereoisomerically enriched product, wherein the product mixture further comprises a Co(II) salen catalyst residue that is active in catalyzing degradation of the stereoisomerically enriched product, and
   contacting the product mixture with at least one oxidizing agent selected from hydrogen peroxide, peracids, persulfates, perborates, perchlorates, oxygen and air to oxidize the Co(II) salen catalyst residue to a Co(III) salen residue in the presence of a complexing agent effective in stabilizing the Co(III) salen residue, wherein the stabilized Co(III) salen residue is less active than the Co(II) salen catalyst residue in catalyzing degradation of the stereoisomerically enriched product.

35. The method of claim 34, wherein the nucleophile comprises water.

36. The method of claim 34, wherein the substrate is a mixture of styrene oxide enantiomers.

37. The method of claim 34, wherein the oxidizing agent comprises air.

38. The method of claim 34, wherein the complexing agent comprises ammonium hydroxide.

39. A method for stereoselective chemical synthesis, comprising:
   reacting water and a mixture of (R)-styrene oxide and (S)-styrene oxide enantiomers in the presence of a chiral, nonracemic Co(III) salen catalyst to produce a product mixture that is stereoisomerically enriched in one of the styrene oxide enantiomers, wherein the product mixture further comprises a Co(II) salen catalyst residue, and
   contacting the product mixture with air to oxidize the Co(II) salen catalyst residue to a Co(III) salen residue in the presence of ammonium hydroxide.

* * * * *